United States Patent [19]

Graham

[11] 4,130,113
[45] Dec. 19, 1978

[54] RETRACTOR
[75] Inventor: Charles M. Graham, Memphis, Tenn.
[73] Assignee: Richards Manufacturing Co., Inc., Memphis, Tenn.
[21] Appl. No.: 750,968
[22] Filed: Dec. 15, 1976
[51] Int. Cl.² ............................................. A61B 17/02
[52] U.S. Cl. .................................. 128/20; 128/303 A
[58] Field of Search ...................... 128/17, 18, 20, 244, 128/3, 303 A, 303 N, 345

[56] References Cited
U.S. PATENT DOCUMENTS

| 2,083,573 | 6/1937 | Morgan | 128/3 |
| 3,572,326 | 3/1971 | Jensen | 128/20 |

FOREIGN PATENT DOCUMENTS

| 542744 | 10/1921 | France | 128/3 |
| 330629 | 6/1930 | United Kingdom | 128/3 |

Primary Examiner—Robert W. Michell
Assistant Examiner—Milford Juten

[57] ABSTRACT

A retractor for opening and holding open an incision to allow a surgeon ready access through the incision during an operation or the like. A plurality of substantially opposed flesh engaging blades for engaging the sides of a surgical incision are pivotally mounted on a body which is provided with an aperture for placement over the surgical incision. A trigger is operatively coupled to the plurality of flesh engaging blades to cause the blades to simultaneously diverge from one another to thereby open the surgical incision and to allow the surgeon access into the surgical incision through the aperture in the body.

7 Claims, 12 Drawing Figures

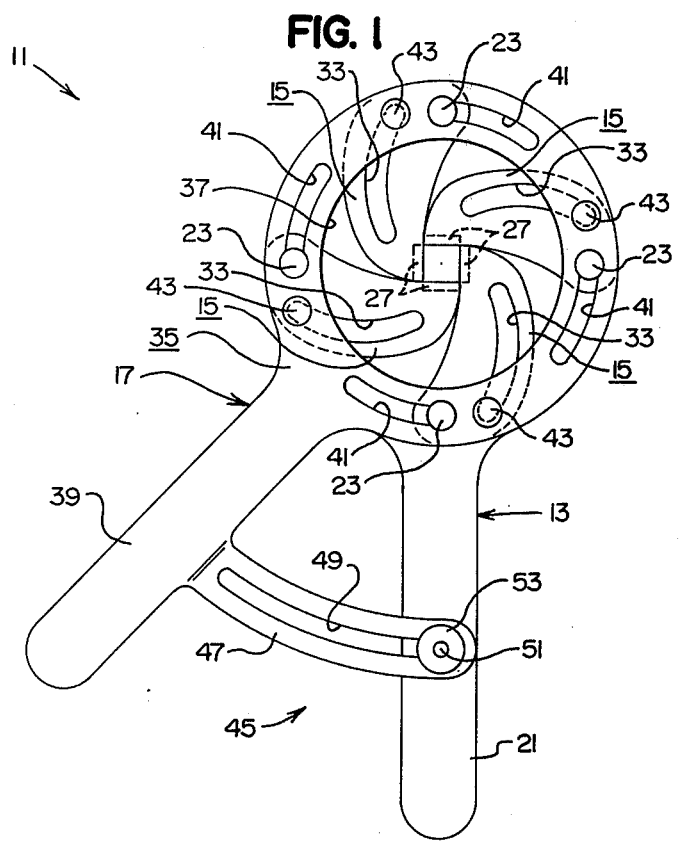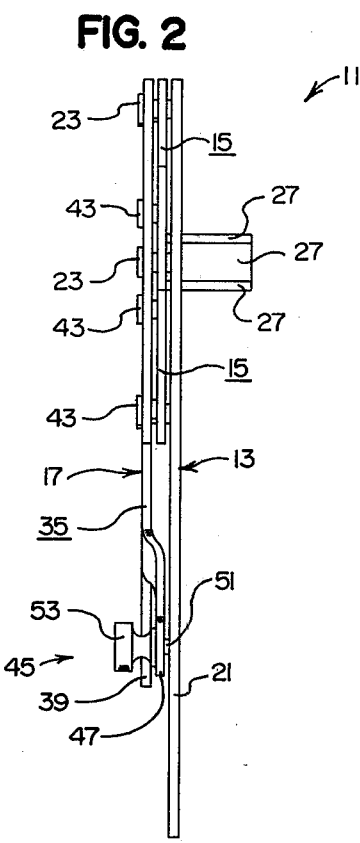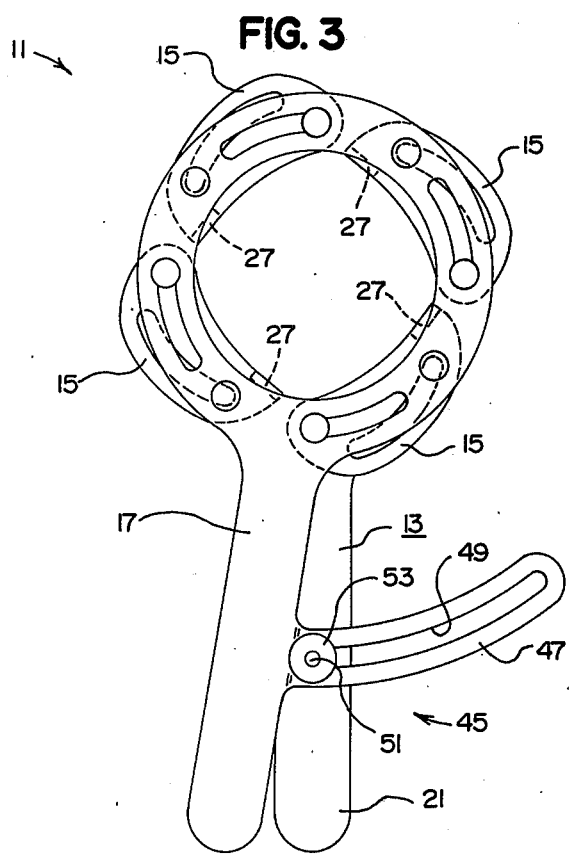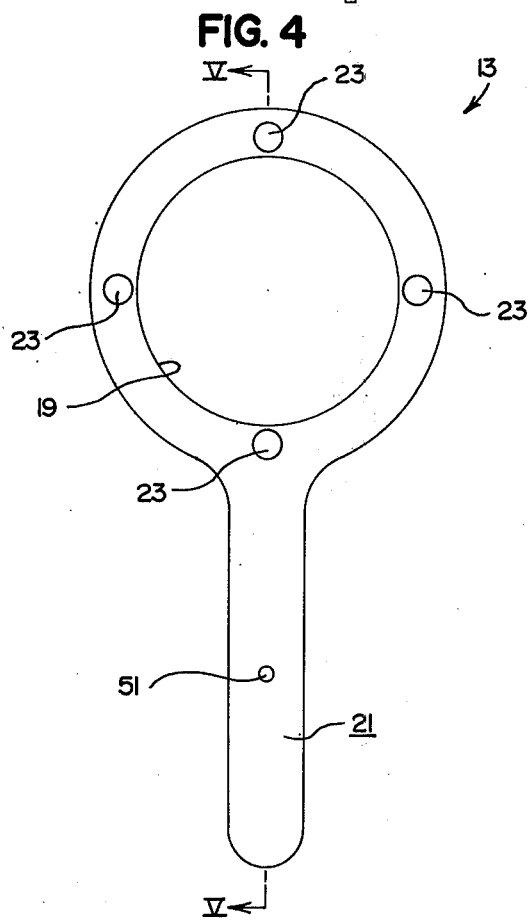

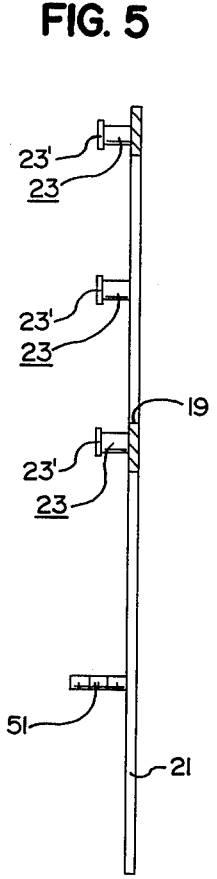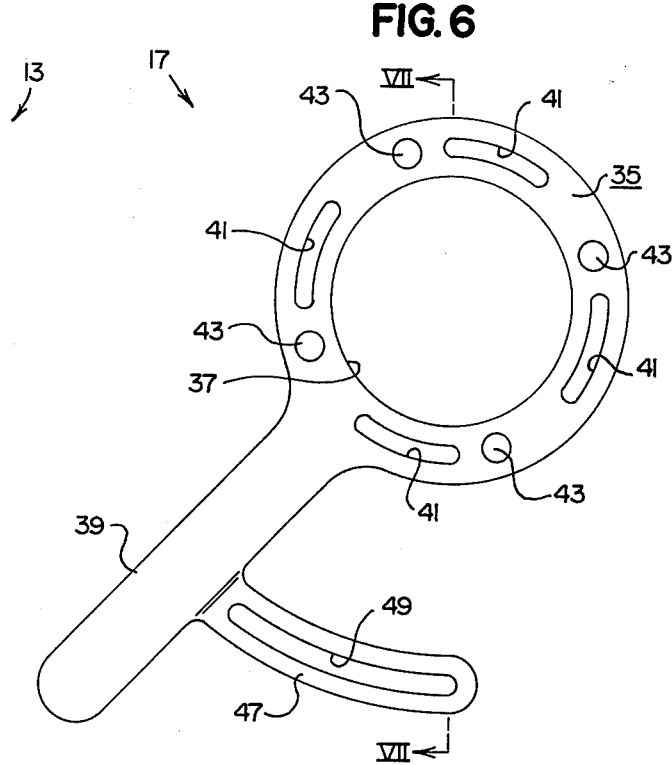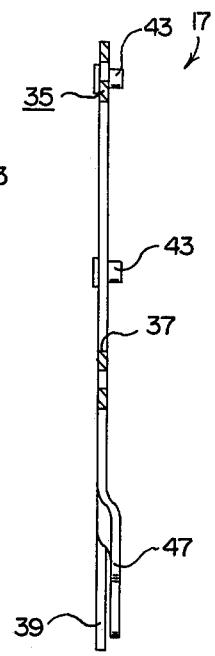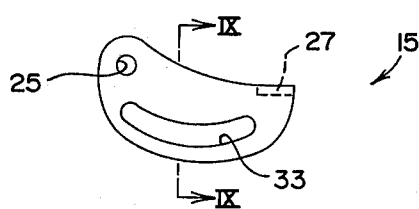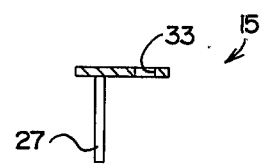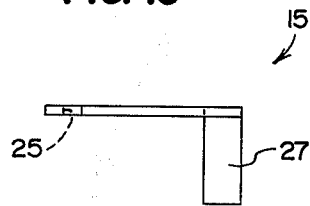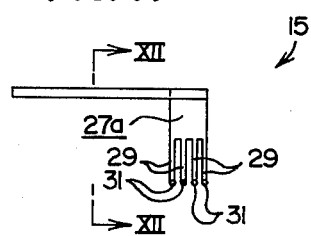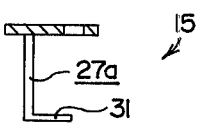

RETRACTOR

BACKGROUND OF THE INVENTION

1. Field of the Invention

This invention relates generally to surgical retractors for opening and holding open a surgical incision.

2. Description of the Prior Art

Various types of retractors have heretofore been developed for opening and holding open surgical incisions or the like to allow a surgeon ready access therethrough. A common type of such retractors consist merely of a rake-like member having a first end provided with a downturned portion for being inserted into a surgical incision and having a second end provided with a handle portion for allowing the user of such a device to manually pull the retractor to spread open the surgical incision. Typically, such a retractor is used in conjunction with a plurality of like retractors and requires a number of assistants to manually open and hold open the surgical incision. One embodiment of this type retractor is disclosed in the Sindelar et al U.S. Pat. No. 3,970,075 and referred to in said patent by the numeral "40". The Sindelar et al patent discloses an anchor apparatus which allows such retractors to be fixedly anchored after they have been pulled to spread open the surgical incision thereby doing away with the need for assistants to hold open the surgical incision once it has been spread open.

Gauthier, U.S. Pat. No. 3,965,890, discloses another type retractor which consists of a frame having a plurality of substantially opposed flesh engaging members movably attached thereto. In this type retractor, the frame is positioned adjacent the surgical incision and the flesh engaging members are positioned so as to engage the surgical incision and are manually and individually moved to spread open the surgical incision. The Gauthier retractor is provided with means to lock the flesh engaging members to the frame in the spread apart position.

None of the above retractors disclose, teach or suggest the present invention.

SUMMARY OF THE INVENTION

The present invention is directed towards improving prior surgical retractors by providing a compact retractor which includes means for causing flesh engaging members to simultaneously spread apart so as to uniformly open a surgical incision.

The retractor of the present invention includes, in general, body means having an aperture therethrough for placement over the surgical incision; a plurality of substantially opposed blade means movably attached to the body means and extending into the aperture of the body means for selectively engaging the incision; and trigger means for causing the plurality of blade means to simultaneously diverge from one another to thereby selectively open the incision.

BRIEF DESCRIPTION OF THE DRAWINGS

FIG. 1 is a front elevational view of the retractor of the present invention shown in a substantially closed position.

FIG. 2 is a side elevational view of the retractor of FIG. 1.

FIG. 3 is a front elevational view of the retractor of the present invention shown in a substantially opened position.

FIG. 4 is a front elevational view of the body means of the retractor of the present invention.

FIG. 5 is a sectional view of the body means of the retractor of the present invention as taken on line V—V of FIG. 4.

FIG. 6 is a front elevational view of the trigger means of the retractor of the present invention.

FIG. 7 is a sectional view of the trigger means of the retractor of the present invention as taken on line VII—VII of FIG. 6.

FIG. 8 is a front elevational view of one of the plurality of blade means of the retractor of the present invention.

FIG. 9 is a sectional view of one of the plurality of blade means of the retractor of the present invention as taken on line IX—IX of FIG. 8.

FIG. 10 is a side elevational view of one of the plurality of blade means of the retractor of the present invention.

FIG. 11 is a side elevational view of a second embodiment of one of the plurality of blade means of the retractor of the present invention.

FIG. 12 is a sectional view of the second embodiment of one of the plurality of blade means of the retractor of the present invention as taken on line XII—XII of FIG. 11.

DESCRIPTION OF THE PREFERRED EMBODIMENT

The retractor 11 of the present invention is primarily for use by a surgeon or the like for spreading open and holding open a surgical incision to allow the surgeon ready access through the incision during an operation or the like. The retractor 11 of the present invention includes, in general, a body means 13, a plurality of blade means 15 movably mounted on the body means 13, and a trigger means 17 operatively coupled to the plurality of blade means 15 for selectively causing the plurality of blade means 15 to simultaneously diverge and/or converge relative to one another.

The body means 13 includes a preferably substantially circular aperture 19 therethrough (see, in general, FIGS. 4 and 5) for placement over the surgical incision. Additionally, the body means 13 preferably includes a grip member 21 for allowing the user of the retractor 11 to grip the body means 13. The body means 13 may be constructed of any substantially rigid material such as, for example, stainless steel and may be constructed in various sizes depending on the specific type surgery or the like the retractor 11 is being used for. The body means 13 is preferably constructed of a substantially thin material so as to enhance the compactness of the retractor 11.

The retractor 11 preferably includes a plurality of post members 23 fixedly attached to the body means 13 substantially adjacent and spaced from one another a substantially equal distance about the aperture 19 through the body means 13 as clearly shown in FIGS. 4 and 5 and for reasons which will hereinafter become apparent. Each of the plurality of post members 23 preferably includes a head portion 23' located on the outer end thereof (see FIG. 5). The retractor 11 preferably includes four post members 23 located substantially 90° apart from one another as clearly shown in FIG. 4.

The plurality of blade means 15 are movably attached to the body means 13 in such a manner so as to extend into the aperture 19 of the body means 13 and are adapted for engaging the surgical incision. More specifically, each of the plurality of blade means 15 is preferably pivotally mounted to one of the plurality of post members 23. That is, each of the plurality of blade means 15 preferably has an aperture 25 therethrough (see FIGS. 8 and 10) for allowing each of the plurality of blade means 15 to be pivotally mounted to one of the plurality of post members 23. Additionally, each of the plurality of blade means 15 preferably includes a downturned flesh engaging portion 27 extending through the aperture 19 of the body means 13 as can be seen in FIG. 2 and for being inserted into the surgical incision to be opened. A second embodiment of the downturned flesh engaging portion of each of the plurality of blade means 15 is shown in FIGS. 11 and 12 and identified by the numeral 27a. In this embodiment, the flesh engaging portions 27a of each of the plurality of blade means 15 includes a plurality of prong-like members 29 adjacent the lower edge thereof (see FIG. 11) for grippingly engaging the flesh surrounding the surgical incision. Additionally, the downturned flesh engaging portion 27a may include a flange-like member 31 adjacent the lower edge thereof (see FIG. 12) for grippingly engaging the flesh surrounding the surgical incision. It should be noted that the flesh engaging portion 27a may include the plurality of prong-like members 29 with or without the flange-like member 31 and, vice versa, may include the flange-like member 31 with or without the plurality of prong-like members 29. When the flesh engaging portion 27a includes both the plurality of prong-like members 29 and the flange-like member 31, each of the plurality of prong-like members 29 is preferably provided with flange member 31 as clearly shown in FIG. 11. More specifically, in this embodiment, the flange-like members 31 consist merely of continuations of each of the plurality of prong-like members 29, bent at substantially right angles to the plurality of prong-like members 29 as clearly shown in FIGS. 11 and 12. Furthermore, the flesh engaging portion 27 may be constructed in various other configurations apparent to those skilled in the art. Each of the plurality of blade means 15 preferably include an elongated, slightly curved slot 33 therethrough as clearly shown in FIG. 8 for reasons which will hereinafter become apparent. The blade means 15 may be constructed of any substantially rigid material such as, for example, stainless steel and may be constructed in various sizes depending on the specific type surgery or the like the retractor 11 is being used for.

The trigger means 17 preferably includes a body member 35 having a substantially circular aperture 37 therethrough substantially the same size as the aperture 19 through the body means 13 and having a grip member 39 for allowing the user of the retractor 11 to grip the body member 35 of the trigger means 17 (see, in general, FIGS. 6 and 7). The body member 35 of the trigger means 17 preferably has a plurality of elongated, slightly curved slots 41 therethrough substantially adjacent and spaced substantially equal distance about the aperture 37 through the body member 35 as clearly shown in FIG. 6 for slidable engagement with the plurality of post members 23 to allow the body member 35 of the trigger means 17 to be movably attached to the body means 15 with the apertures 19, 37 through the body means 13 and the body member 35 of the trigger means 17, respectively, being constantly in substantial alignment with one another as clearly shown in FIGS. 1 and 3. That is, the apertures 19, 37 through the body means 13 and the body member 35 of the trigger means 17 are preferably in substantial alignment with one another when the plurality of blade means 15 are in the completely converged portion as shown in FIG. 1, the completely diverged position as shown in FIG. 3, and any position therebetween. The trigger means 17 also preferably includes a plurality of substantially post-like cam members 43 fixedly attached to the body member 35 thereof for slidable engagement with the elongated slots 33 of the plurality of blade means 15 so that when the body member 35 of the trigger means 17 is rotated relative to the body means 13, the plurality of blade means 15 will be simultaneously pivoted about the plurality of post members 23. The body member 35 of the trigger means 17 may be constructed of any substantially rigid material such as, for example, stainless steel and may be constructed in various sizes depending on the specific type surgery or the like the retractor 11 is being used for. The body member 35 is preferably constructed of a thin, substantially flat material so as to enhance the compactness of the retractor 11.

The retractor 11 preferably includes a lock means 45 for locking the plurality of blade means 15 in a diverged position so as to hold the surgical incision open (see, in general, FIGS. 1, 2 and 3). The lock means 45 may be constructed in any manner apparent to those skilled in the art. For example, the lock means 45 may include an elongated member 47 fixedly attached to the grip member 39 of the body member 35 of the trigger means 17 substantially as shown in FIGS. 1, 2, 3, 6 and 7 having an elongated, slightly curved slot 49 therethrough; may include a screwlike member 51 fixedly attached to the grip member 21 of the body means 13 substantially as shown in FIGS. 1, 2, 3, 4 and 5 for extending through the slot 49 in the elongated member 47; and may include a nutlike member 53 for screwably mounting on the screwlike member 51 to selectively lock the body means 13 and trigger means 17 together in a manner which should be apparent to those skilled in the art.

The preferred manner of using the retractor 11 of the present invention is quite simple. First, with the grip members 21, 39 of the body means 13 and the body member 35 of the trigger means 17 spread apart from one another as shown in FIG. 1 so that the flesh engaging portions 27 of the plurality of blade means 15 will be substantially adjacent one another, the flesh engaging portions 27 of the plurality of blade means 15 are inserted into the surgical incision at the location where it is desired to open the surgical incision. Next, the grip members 21, 39 of the body means 13 and the body member 35 of the trigger means 17 are manually moved towards one another so as to cause the plurality of blade means 15 to simultaneously diverge from one another in a manner somewhat similar to the iris of the eye and the jaw members of a universal chuck. Once the surgical incision has been opened sufficiently, the nutlike member 53 of the lock means 45 is tightened so as to lock the plurality of blade means 15 in the diverged position (see FIG. 3) so as to hold the surgical incision open. The surgeon then has access through the apertures 19, 37 in the body means 13 and the body member 35 of the trigger means 17 into the opened surgical incision.

As thus constructed and used, the present invention provides a surgical retractor which allows simultaneous and uniform adjustment of a surgical incision, which does the work of a plurality of hand held retractors, which does not require the aid of surgical assistants to open and hold open a surgical incision, and which is compact so as not to interfere with the surgery or the like.

Although the invention has been described and illustrated with respect to a preferred embodiment thereof, it is not to be so limited since changes and modifications may be made therein which are within the full intended scope of the invention.

I claim:

1. A surgical retractor for holding open a surgical incision, said retractor comprising:
   (a) body means having an aperture therethrough for placement over the incision;
   (b) a plurality of post members fixedly attached to said body means substantially adjacent and spaced substantially equal distance about said aperture through said body means;
   (c) a plurality of substantially opposed blade means movably attached to said body means and extending into said aperture through said body means blade means, portions on said for being inserted into and engaging the incision to be held open, each of said plurality of blade means being pivotally mounted to one of said plurality of post members, each of said plurality of blade means including an elongated, slightly curved slot therethrough; and
   (d) trigger means for causing said plurality of blade means to simultaneously diverge from one another and pivot about said plurality of post members to thereby open the incision, said trigger means including a body member having an aperture therethrough substantially the same size as said aperture through said body means, said body member of said trigger means having a plurality of elongated, slightly curved slots therethrough for slidable engagement with said plurality of post members to allow said body member of said trigger means to be movably attached to said body means with said apertures through said body means and said body member of said trigger means being constantly in substantial alignment with one another, said trigger means including a plurality of cam members fixedly attached to said body member thereof for slidable engagement with said elongated slots of said plurality of blade means so that when said body member of said trigger means is rotated relative to said body means, said plurality of blade means will be simultaneously pivoted about said plurality of post members.

2. A surgical retractor for holding open a surgical incision, said retractor comprising:
   (a) body means having an aperture therethrough for placement over the incision;
   (b) a plurality of post members fixedly attached to said body means substantially adjacent and spaced substantially equal distance about said aperture through said body means;
   (c) a plurality of substantially opposed blade means movably attached to said body means and extending into said aperture through said body means for engaging the incision, each of said plurality of blade means being pivotally mounted to one of said plurality of post members, each of said plurality of blade means including an elongated, slightly curved slot therethrough, each of said plurality of blade means including a downturned flesh engaging portion for being inserted into the incision to be held open; and
   (d) trigger means for causing said plurality of blade means to simultaneously diverge from one another and pivot about said plurality of post members to thereby open the incision, said trigger means including a body member having an aperture therethrough substantially the same size as said aperture through said body means, said body member of said trigger means having a plurality of elongated, slightly curved slots therethrough for slidable engagement with said plurality of post members to allow said body member of said trigger means to be movably attached to said body means with said apertures through said body means and said body member of said trigger means being constantly in substantial alignment with one another, said trigger means including a plurality of cam members fixedly attached to said body member thereof for slidable engagement with said elongated slots of said plurality of blade means so that when said body member of said trigger means is rotated relative to said body means, said plurality of blade means will be simultaneously pivoted about said plurality of post members.

3. The retractor of claim 2 in which each of said flesh engaging portions of said plurality of blade means includes a flange-like member and adjacent the lower edge thereof for grippingly engaging the flesh surrounding the incision to be held open.

4. The retractor of claim 2 in which each of said flesh engaging portions of said plurality of blade means includes a plurality of prong-like members adjacent the lower edge thereof for grippingly engaging the flesh surrounding the incision to be held open.

5. The retractor of claim 1 in which is included lock means for locking said plurality of blade means in a diverged position so as to hold the incision open.

6. A surgical retractor for opening and holding open a surgical incision, said surgical retractor comprising:
   (a) body means having a substantially circular aperture therethrough for placement over the surgical incision and including a grip member for allowing the user of said surgical retractor to grip said body means;
   (b) a plurality of post members fixedly attached to said body means substantially adjacent and spaced substantially equal distance about said aperture through said body means;
   (c) a plurality of blade means extending into said aperture through said body means, each of said plurality of blade means being pivotally mounted to one of said plurality of post members and including a downturned flesh engaging portion for being inserted into the surgical incision to be opened and held opened, each of said plurality of blade means including an elongated, slightly curved slot therethrough;
   (d) trigger means for causing said plurality of blade means to simultaneously pivot about said plurality of post members to thereby open the surgical incision, said trigger means including a body member having a substantially circular aperture therethrough substantially the same size as said aperture through said body means and having a grip member for allowing the user of said surgical retractor to grip said body member of said trigger means, said body member of said trigger means having a plurality of elongated, slightly curved slots therethrough for slidable engagement with said plurality of post members to allow said body member of said trigger means to be movably attached to said body means with said apertures through said body means and said body member of said trigger means being constantly in substantial alignment with one another, said trigger means including a plurality of cam members fixedly attached to said body member thereof for slidable engagement with said elongated slots of said plurality of blade means so that when said body member of said trigger means is rotated relative to said body means, said plurality of blade means will be simultaneously pivoted about said plurality of post members; and (e) lock means for locking said plurality of blade means in a diverged position so as to hold the surgical incision open.

7. An improved surgical retractor of the type including a body means having an aperture therethrough for placement over a surgical incision and including a plurality of substantially opposed blade means movably attached to said body means and extending into said apertures of said body means, portion on said blade means for extending into and engaging the surgical incision, wherein the improvement comprises: a plurality of post members fixedly attached to said body means substantially adjacent and spaced substantially equal distance about said aperture through said body means; each of said plurality of blade means being pivotally mounted to one of said plurality of post members, each of said plurality of blade means including an elongated, slightly curved slot therethrough; and trigger means for causing said plurality of blade means to simultaneously diverge from one another and pivot about said plurality of post members to thereby open the surgical incision, said trigger means including a body member having an aperture therethrough substantially the same size as said aperture through said body means, said body member of said trigger means having a plurality of elongated, slightly curved slots therethrough for slidable engagement with said plurality of post members to allow said body member of said trigger means to be movably attached to said body means with said apertures through said body means and said body member of said trigger means being constantly in substantial alignment with one another, said trigger means including a plurality of cam members fixedly attached to said body member thereof for slidable engagement with said elongated slots of said plurality of blade means so that when said body member of said trigger means is rotated relative to said body means, said plurality of blade means will be simultaneously pivoted about said plurality of post members.

* * * * *